United States Patent [19]

Akiyama

[11] Patent Number: 5,220,002
[45] Date of Patent: Jun. 15, 1993

[54] DEACETYLCOLCHICINE DERIVATIVES

[75] Inventor: Kiyoshi Akiyama, Komatsu, Japan

[73] Assignee: Ohgen Research Laboratories, Ltd., Ishikawa, Japan

[21] Appl. No.: 810,883

[22] Filed: Dec. 20, 1991

[30] Foreign Application Priority Data

Dec. 25, 1990 [JP] Japan .................. 2-413683
Dec. 25, 1990 [JP] Japan .................. 2-419162

[51] Int. Cl.$^5$ .................... A61K 31/70; A61K 47/48; C07H 7/00; C07C 235/14
[52] U.S. Cl. .................... 536/187; 514/629; 514/630; 514/676
[58] Field of Search .................. 514/629, 630, 676; 536/18.7

[56] References Cited

U.S. PATENT DOCUMENTS 4,533,675  8/1985  Brosai et al. .................. 514/480
4,692,463  9/1987  Brosai .......................... 514/463
4,904,697  2/1990  Sunkara et al. ................ 514/630

FOREIGN PATENT DOCUMENTS 0382411  8/1990  European Pat. Off. .
1175407  3/1959  France .

OTHER PUBLICATIONS

Raffauf et al., J. Am. Chem. Soc., vol. 75, pp. 5292-5294 (1953).
Ueno, J. Pharm. Soc. Japan, vol. 73, pp. 1238-1242 (1953).
Shiau et al., J. Pharm. Sci., vol. 67, No. 3, pp. 394-397 (1978).
Clark et al., Life Sciences, vol. 26, pp. 833-836 (1980).
Iorio et al., Can. J. Chem., vol. 59 (1981) pp. 283-284 (1981).

*Primary Examiner*—Ronald W. Griffin
*Attorney, Agent, or Firm*—Wenderoth, Lind & Ponack

[57] ABSTRACT

Deacetylcolchicine derivatives represented by the formula

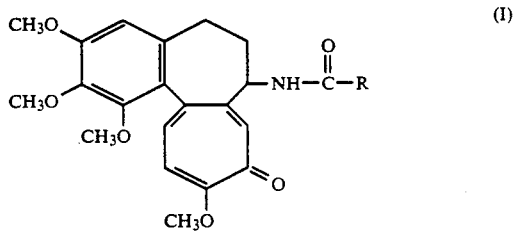

wherein R denotes a residue obtained by removing COOH from a $C_3$-$C_7$ sugar carboxylic acid, and a hydroxyl group present in the residue may properly be protected with a protecting group of the hydroxyl group.

Said deacetylcolchicine derivatives have less toxicity and strong effect for inhibiting proliferation of tumor cells, and are expected to be used as an antitumor agent.

6 Claims, No Drawings

DEACETYLCOLCHICINE DERIVATIVES

DETAILED DESCRIPTION OF THE INVENTION

This invention relates to novel deacetylcolchicine derivatives. More specifically, this invention relates to deacetylcolchicine derivatives represented by the formula

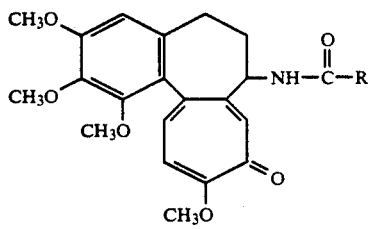

wherein R denotes a residue obtained by removing COOH from a $C_3$-$C_7$ sugar carboxylic acid, and a hydroxyl group present in the residue may properly be protected with protecting groups for the hydroxyl group.

It was already known that colchicine represented by the formula

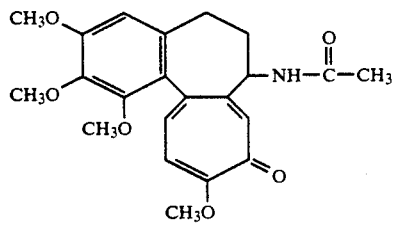

has pharmaceutical activity to tumor cells, gout, etc. [See Colchicine in Agriculture, Medicine, Biology and Chemistry (Iowa Stage College Press Ames, Iowa, 1955.]

Colchicine shows, however, high toxicity, and has been completely neglected by the advent of demecolchicine (deacetyl-N-methylcolchicine) which has been later discovered [Chem. Engng. News, 37,n No. 41, 67 (1959)].

The present inventors have therefore made assiduous investigations to look for colchicine derivatives having less toxicity and better antitumor activity, and consequently have found that deacetylcolchicine derivatives represented by formula (I) show a high effect for inhibiting proliferation of tumor cells and are expected to be used as an antitumor agent. This finding has led to completion of the present invention.

A "residue obtained by removing COOH from a $C_3$-$C_7$ sugar carboxylic acid", which is represented by R, includes a monovalent residue (hereinafter referred to as a "sugar residue") obtained by removing COOH from a $C_3$-$C_7$ monosaccharide carboxylic acid such as glyceric acid, ribose carboxylic acid, glucuronic acid, gluconic acid or glucoheptanoic acid. Examples thereof are as follows.

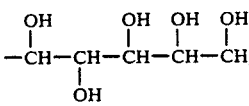

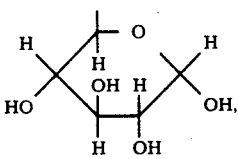

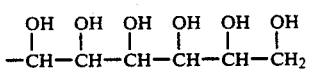

At least part of the plural hydroxyl groups present in the sugar residue may properly be protected with a protecting group for the hydroxyl group. Examples of the protecting group are acyl groups such as acetyl, propionyl, butylyl, pivaloyl and benzoyl; and acetal and ketal groups represented by the following formulas:

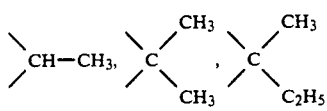

The compound of this invention can be formed, for example, by subjecting deacetylcolchicine represented by the formula

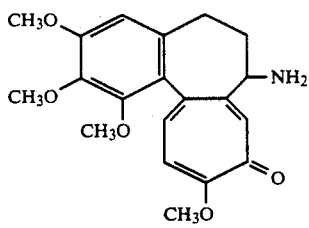

to amidation using a sugar carboxylic acid represented by the formula

<p style="text-align:right">R—COOH    (III)</p> wherein R is as defined above,
or its reactive derivatives.

Amidation of deacetylcolchicine with the sugar carboxylic acid of formula (III) or its reactive derivatives (e.g., halides and active esters) can be carried out by an amidation reaction known per se in peptide chemistry.

For instance, the compound of this invention can be produced by reacting deacetylcolchicine with the sugar carboxylic acid halide of formula (III) in the presence of a base. The above reaction can be performed at a temperature of usually about 0° C. to about 30° C., preferably about 0° C. to about room temperature. The amount of the halide is not strictly limited; it is usually 1 to 1.5 mols, preferably 1 to 1.2 mols per mol of deacetylcolchicine. Examples of the base are tertiary amines such as triethylamine and pyridine; and alkali metal (hydrogen) carbonates such as sodium carbonate, sodium hydrogen carbonate, potassium carbonate and potassium hydrogen carbonate. The amount of the base is usually 1 to 1.5 mols, preferably 1 to 1.2 mols per mol of deacetylcolchicine.

The above reaction can usually be effected in an inert solvent. Examples of the solvent are halogenated hydrocarbons such as methylene chloride, chloroform, carbon tetrachloride, dichloroethylene, and trichloroethylene; aliphatic ethers such as ethyl ether and methyl cellosolve; and aromatic hydrocarbons such as benzene and toluene.

The compound of this invention can be produced by directly reacting deacetylcolchicine with the sugar carboxylic acid in the presence of a condensation agent such as dicyclohexylcarbodiimide (DCC), or by reacting deacetylcolchicine with an ester (such as a methyl ester, an ethyl ester or a butyl ester) of the sugar carboxylic acid of formula (III).

The thus obtained compound of this invention can be separated and purified by a method known per se, such as extraction, chromatography, crystallization, or a combination thereof.

In case of the compound of this invention wherein the protecting group for the hydroxyl group is present in the sugar residue represented by R, the protecting group may be removed by a deprotection reaction, e.g., hydrolysis, as required.

In the aforesaid reaction, deacetylcolchicine used as a starting material is a compound known per se [see J. Am. Chem. Soc., 75, 5292 (1953)] and can be formed by a known method. Or it can be formed by reacting colchicine represented by the formula

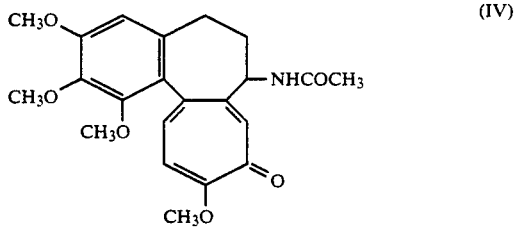

(IV)

with trialkyloxonium fluoroborate and then treating the reaction mixture with water according to a method which the present inventors have developed afresh.

The reaction of colchicine with trialkyloxonium fluoroborate can be carried out at a temperature of about 0° C. to about 30° C., preferably about 0° C. to about room temperature in an inert organic solvent. Examples of the inert organic solvent are halogenated hydrocarbons such as methylene chloride, chloroform, carbon tetrachloride, dichloroethylene, and trichloroethylene; aliphatic ethers such as ethyl ether and methyl cellosolve; and aromatic hydrocarbons such as benzene and toluene.

The trialkyloxonium fluoroborate being reacted with colchicine is a compound represented by the formula $$(R')_3O^+ \cdot BF_4^-$$ (V)

wherein R' denotes an alkyl group.
Concretely, triethyloxonium fluoroborate $[(C_2H_5)_3O^+ \cdot BF_4^-]$ known as a Meerwein reagent is preferable.

The amount of the trialkyloxonium fluoroborate is usually 1 to 2 mols, preferably 1 to 1.5 mols per mol of colchicine.

It is presumed that the reaction of colchicine with trialkyloxonium fluoroborate gives a compound represented by the formula,

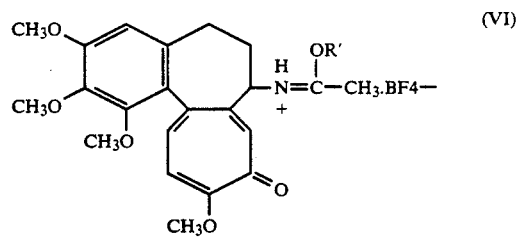

(VI)

wherein R' is as defined above.

Deacetylcolchicine of formula (II) can be formed by treating the compound of formula (VI) as such with water. The treatment with water can be effected by stirring at a temperature of usually about 0° C. to about 30° C., especially room temperature for about 30 minutes to about 3 hours. The amount of water is at least 1 mol, usually an excessive amount per mol of colchicine used as a starting material.

Deacetylcolchicine is thereby formed in a state dissolved in an aqueous phase and can be separated from the aqueous phase and purified by a method known per se. For example, deacetylcolchicine can be separated by rendering the aqueous layer alkaline in the range of pH of about 9 to about 10 with the addition of an alkali such as sodium hydroxide, potassium hydroxide, sodium carbonate or sodium hydrogen carbonate, and then conducting extraction in the presence of an organic solvent, for example, a halogenated hydrocarbon such as methylene chloride, chloroform, carbon tetrachloride, dichloroethylene or trichloroethylene; an aliphatic ether such as ethyl ether or methyl cellosolve; or an aromatic hydrocarbon such as benzene or toluene.

The thus separated deacetylcolchicine can be purified, for example, by converting it into a tartrate salt or a malate salt.

The deacetylcolchicine derivatives of formula (I) provided by this invention exhibit excellent anti-tumor activity as is clear from the results of the in vitro or in vivo test on tumor cells which will be described below.

TEST EXAMPLE 1

In Vitro Tumor Cell Proliferation Inhibiting Test $2 \times 10^5$ Adriamycin-resistant mouse leukemic cells P388/ADR are suspended in a RPMI 1640 culture medium containing 10% of a bovine fetal serum, and cultured for 2 days in the presence of a test compound (the test compound is dissolved in dimethyl sulfoxide such that the concentration becomes 1 mg/ml, and this is diluted with a phosphate buffer solution). An influence on cell proliferation is investigated, and 50% proliferation inhibitory concentration: $IC_{50}$ value (μg/ml) is determined. The results are shown in Table 1.

TABLE 1

| Test compound* | $IC_{50}$ |
|---|---|
| Compound 1a | 0.036 |
| Compound 1b | 0.066 |
| Compound 4 | 0.034 |
| Compound 5 | 0.037 |

*Compound numbers have the meanings described later in Examples.

TEST EXAMPLE 2

In Vivo Test on Sarcoma 180 Ascites Tumor Transplanted Mice $1 \times 10^6$ Sarcoma 180 cells are transplanted in an abdominal cavity of each of 6-week old ddY male mice. Over 7 days after the first day of transplantation of tumor cells in groups each consisting of 6 mice, the test compound (which is dissolved in propyplene glycol and diluted with a phosphate buffer solution such that the final concentration of propylene glycol becomes 20% or less) is administered in the abdominal cavity once a day, and an average number of survival days and percent prolongation* are measured. The results are shown in Table 2.

*Percent prolongation =

$$\frac{\text{(Average number of survival days in administered group)} - \text{(Average number of survival days in control group)}}{\text{(Average number of survival days in control group)}} \times 100$$

TABLE 2

| Test compound | Dose (mg/kg i.p) | Average number of survival days (mean ± SD) | Percent prolongation (%) | Cured example |
| --- | --- | --- | --- | --- |
| Compound 1a | 2.5 | 54.2 ± 11.6 | 333 | 4 |
| | 1.25 | 47.2 ± 11.5 | 277 | 2 |
| | 0.63 | 47.7 ± 11.1 | 281 | 1 |
| | 0.31 | 36.0 ± 8.0 | 188 | |
| Compound 1b | 5 | 57.0 ± 5.3 | 356 | 4 |
| | 2.5 | 57.0 ± 7.3 | 356 | 5 |
| | 1.25 | 42.5 ± 15.4 | 240 | 1 |
| | (20% propylene glycol) | 14.3 ± 3.3 | 14.7 | 0 |
| | (Control: untreated) | 12.5 ± 4.8 | — | 0 |

TEST EXAMPLE 3

In Vivo Test on Sarcoma 180 Solid Tumor Transplanted Mice $2 \times 10^6$ Sarcoma 180 cells are transplanted subcutaneously in the back of each of 6-week old ddY female mice. Over 10 days from the 6th day after the tumor transplantation in groups each consisting of 6 mices, the test compound (which is dissolved in propylene glycol and diluted with a phosphate buffer solution such that the final concentration of propylene glycol becomes 20% or less) is continuously administered in the abdominal cavity once a day. Thirty days after the tumor transplantation, the tumor is taken out. Its weight is measured, and an average tumor weight and percent inhibition* are measured. The results are shown in Table 3.

*Percent inhibition =

$$\frac{\text{(average tumor weight in control group)} - \text{(Average tumor weight in administered group)}}{\text{(Average tumor weight in control group)}} \times 100$$

TABLE 3

| Test compound | Dose (µg/kg i.p.) | Average tumor weight (mean ± SD, g) | Percent inhibition (%) |
| --- | --- | --- | --- |
| Compound 1a | 5.0 | 0.60 ± 0.52 | 57.4 |
| | 2.5 | 0.63 ± 0.51 | 55.3 |
| | 1.25 | 0.88 ± 0.78 | 47.6 |
| | 0.625 | 0.71 ± 0.38 | 49.6 |
| Control | (20% propylene glycol) | 1.41 ± 0.58 | — |

TEST EXAMPLE 4

Acute Toxicity Test

The test compound is administered to each 5-week old ddY male mouse, and mortality is observed for 1 week. A 50% lethal dose ($LD_{50}$) is calculated from the number of mice died in each group by a Litchfield-Wilcoxon method. The test compound (compound (a)) is suspended in 10% propylene glycol. Ten dilution gradients are prepared from the maximum concentration 80 mg/kg at a ratio of 1.2, and the test is carried out.

TABLE 4

| Administration method | $LD_{50}$ (mg/kg) |
| --- | --- |
| intraperitoneal | 42 (reliable limit 37.0–47.7) |
| intravenous | 38 (reliable limit 34.3–42.2) |

From the above test results, it follows that the compound of this invention has high inhibitory activity to tumor cells and is expected to be used as an antitumor agent.

When the compound of this invention is used in treatment and therapy of tumors as an antitumor agent, said compound can be administered either orally or parenterally (e.g., intravenously, intramuscularly, subcutaneously or intrarectally). The dose of the compound can vary over a wide range depending on conditions of diseases, sex and weight of patients, administration routes, doctor's diagnosis, and the like. It is usually 1 to 20 mg/kg. In case of the oral administration, the suitable dose is 5 to 10 mg/kg; in case of the intravenous injection, it is 2 to 4 mg/kg.

The compound of this invention can be formulated into tablets, granules, powders, capsules, syrups, injections, drips, or suppositories. The formulation can be carried out according to a method known per se by blending the compound of this invention with a pharmaceutically acceptable carrier or diluent. Examples of the carrier or the diluent are water, ethanol, starch, lactose, sucrose, glucose, mannitol, silica, carboxymethyl cellulose, alginate, gelatin, polyvinyl pyrrolidone, glycerol, agar, calcium carbonate, paraffin, kaolin, talc, calcium stearate, magnesium stearate, and polyethylene glycol.

This invention is illustrated more specifically by the following Examples.

EXAMPLE 1

Production of Deacetylcolchicine

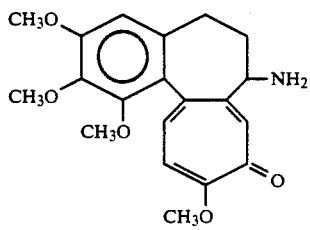

Four grams (10 mmols) of colchicine were dissolved in anhydrous methylene chloride and cooled to 0° C., and 15 mmols of a methylene chloride solution of triethyloxonium fluoroborate (Meerwein reagent) was added dropwise. The solution was stirred at 0° C. for 1 hour and further at room temperature for 5 hours. Thirty milliliters of water were added to the reaction mixture, and the resulting solution was stirred for 1 hour. After the stirring, an aqueous layer was separated with a funnel. A methylene chloride layer was further extracted five times with 50 ml of water. The methylene chloride layer was dried over magnesium sulfate and used to recover unreacted colchicine. The aqueous layer was adjusted to pH of 10 with 1N sodium hydroxide and extracted with chloroform. The chloroform layer was dried over magnesium sulfate and then concentrated with an evaporator. The residue was dissolved in 30 ml of ethanol, and 1 g of D-tartaric acid was added, followed by heating the mixture for 1 hour. After the mixture was cooled to room temperature, the precipitate was filtered. The obtained tartrate salt was dried with a desiccator (decomposed at a melting point of 219° to 220° C.).

The tartrate salt was dissolved in 50 ml of water, readjusted to pH of 10 with 1N sodium hydroxide, and extracted with chloroform. The extract was dried over magnesium sulfate and concentrated under reduced pressure with an evaporator to obtain 1.38 g of oily deacetylcolchicine. The yield was 39%.

Unreacted colchicine can be recovered from a benzene-acetone solvent eluted portion by silica gel column chromatography of the initial methylene chloride layer (1.71 g). The yield of deacetylcolchicine given by subtracting this is 61%.

EXAMPLE 2

Deacetylcolchicine-glyceric Acid Acetonideamide (Compound 1)

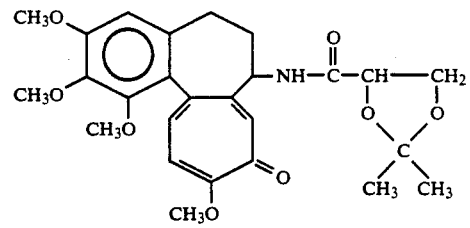

Potassium glyceride acetonide (3.60 g, 20 mmols) was suspended in 30 ml of anhydrous ether, and an ether (5 ml) solution of 2.40 g (20 mmols) of thionyl chloride was added dropwise to the suspension. After the dropwise addition, the mixture was refluxed for 3 hours. After the mixture was cooled to room temperature, the precipitate was filtered by suction, and the filtrate was concentrated under reduced pressure. Anhydrous methylene chloride was added to the residue and dissolved.

Meanwhile, 2.96 g (8.3 mmols) of deacetylcolchicine and 2.02 g (20 mmols) of triethylamine were dissolved in 30 ml of methylene chloride. The mixture was cooled to 0° C., and the above methylene chloride solution of glyceric acid chloride was added dropwise. After stirring at 0° C. for 3 hours, the methylene chloride solution was washed with a sodium hydrogen carbonate aqueous solution. The methylene chloride layer was dried over magnesium sulfate and then concentrated under reduced pressure. The residue was separated by silica gel column chromatography, and 1.11 g of a product (compound 1a: L-isomer) was obtained from a benzeneacetone (5:1) eluted portion. The yield was 28% and m.p. 251° to 253° C. (decomposed).

Further, 0.58 g of a second product (compound 1b: D-isomer) was obtained from a benzene-acetone (5:2) eluted portion. The yield was 14%.

Compound 1a: IR (KBr): 3250 cm$^{-1}$ (NH), 1670 cm$^{-1}$ (C=O), 1250 cm$^{-1}$ (—O—);

NMR (DCDl$_3$):=1.40 (3H,s), 1.60 (3H,s), 1.69-2.67 (4H,m), 3.62 (3H,s), 3.87 (3H,s), 3.91 (3H,s), 3.93 (3H,s), 4.00-4.50 (4H,s), 6.49-7.29 (4H,m). [0046]

Compound 1b: IR (KBr): 3250 cm$^{-1}$ (NH), 1670 cm$^{-1}$ (C=O), 1250 cm$^{-1}$ (—O—);

NMR (DCDl$_3$):=1.37 (3H,s), 1.46 (3H,s), 1.69-2.67 (4H,m), 3.62 (3H,s), 3.86 (3H,s), 3.91 (3H,s), 3.97 (3H,s), 4.00-4.50 (4H,s), 6.49-7.29 (4H,m).

EXAMPLE 3

Deacetylcolchicine-glyceric acid amide
[N-(5,6,7,9-tetrahydro-1,2,3,10-tetramethoxy-4-oxobenzo[a]heptalen-7-yl)glyceroamide](Compound 2)

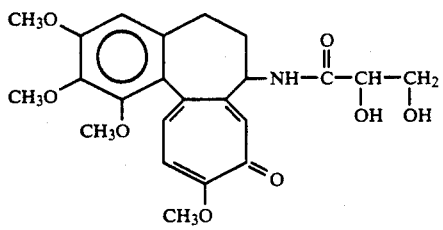

Ten milliliters of 5% hydrochloric acid were added to a methanol (30 ml) solution of 0.94 g (2 mmols) of deacetylcolchicine-glyceric acid acetonideamide (compound 1) obtained in Example 2, and they were stirred at room temperature for 5 hours. After stirring, 200 ml of chloroform was added, and the mixture was washed with a sodium hydrogen carbonate aqueous solution and a saturated NaCl aqueous solution. The chloroform layer was dried over magnesium sulfate, and then concentrated under reduced pressure. The residue was separated by silica gel column chromatography. The elution with a benzene-aceton (1:2) solvent afforded 0.45 g of the above-captioned compound (compound 2; D,L-mixture). The yield was 52% and m.p. 48° to 50° C.

IR (KBr): 3350 cm$^{-1}$ (OH), 1660 cm$^{-1}$ (C=O), 1280 cm$^{-1}$ (—O—);

NMR (DCDl$_3$):=1.87–2.64 (4H,m), 3.62 (3H,s), 3.87 (3H,s), 3.91 (3H,s), 3.96 (3H,s), 3.56–4.84 (6H,m), 6.51–7.58 (4H,m), 7.9 (1H,brs).

EXAMPLE 4

Deacetylcolchicine-glucuronic acid tetraacetateamide (Compound 3)

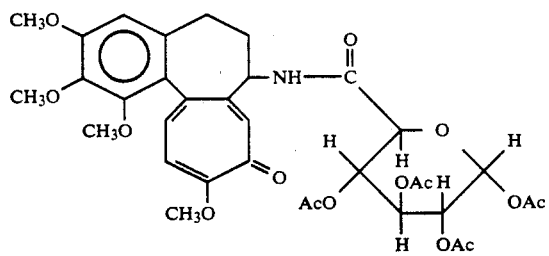

Thionyl chloride (1.19 g, 10 mmols) was added to 30 ml of a chloroform solution of 1.81 g (5 mmols) of glucuronic acid tetraacetate, and the mixture was refluxed for 3 hours. After the mixture was cooled to room temperature, the solvent and excess thionyl/chloride were removed under reduced pressure. The residual acid chloride was dissolved in 10 ml of methylene chloride. Meanwhile, 1.78 g (5 mmols) of deacetylcolchicine and 0.60 g (6 mmols) of triethylamine were dissolved in 30 ml of methylene chloride and cooled to 0° C. To the mixture was added the above acid chloride, and stirring was conducted at 0° C. for 1.5 hours and at room temperature for 1.5 hours. The reaction mixture was washed with a sodium hydrogen carbonate aqueous solution and then dried over magnesium sulfate. After the solvent was concentrated, the residue was separated by silica gel column chromatography. By the elution with a benzene-acetone (11:3) solvent, 1.30 g of the above-captioned compound (compound 3) was obtained. The yield was 37% and m.p. 145° to 147° C. (decomposed).

IR (KBr): 1750 cm$^{-1}$ (OH), 1680 cm$^{-1}$ (C=O);

NMR (DCDl$_3$):=1.91 (3H,s), 1.96 (3H,s), 2.00 (2H,s), 2.09 (3H,s), 2.10–2.64 (4H,m), 3.58 (3H,s), 3.87 (3H,s), 3.89 (6H,s), 4.00–4.22 (1H,m), 5.00–5.38 (4H,m), 5.80–5.89 (1H,m), 6.47–7.53 (4H,m).

EXAMPLE 5

Deacetylcolchicine-glucuronic acid diacetateamide (Compound 4)

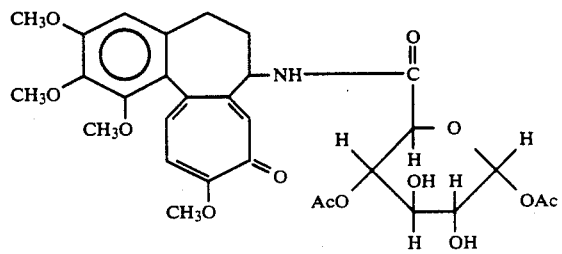

The above-captioned compound was formed as in Example 4 except using 3.62 g (13 mmols) of glucuronic acid diacetate, 1.71 g (15 mmols) of thionyl chloride, 2.89 g (8 mmols) of deacetylcorchicine and 1.52 g (15 mmols) of triethylamine. The amount was 1.67 g and the yield 35%.

NMR (DCDl$_3$):=2.15 (6H,s), 2.26–2.71 (4H,m), 3.64 (3H,s), 3.89 (6H,s), 3.98 (3H,s), 3.37–4.48 (8H,m), 6.53–7.81 (4H,m).

EXAMPLE 6

Deacetylcolchicine-glucuronic acid amide
[N-(5,6,7,9-tetrahydro-1,2,3,10-tetramethoxy-9-oxobenzo[a]heptalen-7-yl)glucuroneamide] (Compound 5)

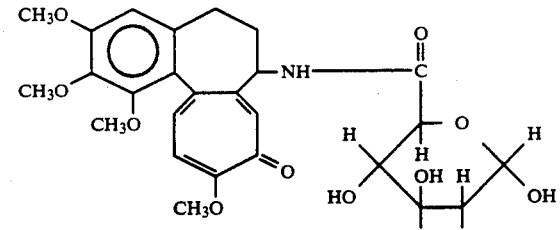

Deacetylcolchicine-glucuronic acid diacetateamide (compound 4) (1.52 g, 2.5 mmols) obtained in Example 5 was dissolved in 30 mmols of methanol and cooled to 0° C. Five milliliters of 1N sodium hydroxide were added dropwise thereto, and the mixture was stirred at 0° C. for 1 hour. The mixture was adjusted to pH of 7 with dilute hydrochloric acid, and concentrated under reduced pressure. Chloroform was added to the residue, and the precipitate was filtered, followed by separating the filtrate via silica gel column chromatography. As a result, 0.93 g of the above-captioned compound (compound 5) was obtained from a benzene-methanol (5:1) eluted portion. The yield was 73% and m.p. 53° to 57° C.

NMR (DCDl$_3$):=2.22–2.67 (4H,m), 2.96–3.27 (4H,m), 3.62 (3H,s), 3.87 (6H,s), 3.93 (3H,s), 3.50–4.22 (6H,m), 6.48–7.78 (4H,m).

EXAMPLE 7

Deacetylcolchicine-gluconic acid pentaacetateamide (Compound 6)

Thionyl chloride (1.50 g, 13 mmols) was added to 30 ml of a chloroform solution containing 2.57 g (6.3 mmols) of gluconic acid pentaacetate, and they were refluxed for 3 hours. After the mixture was cooled to room temperature, the solvent and excess thionyl/chloride were removed under reduced pressure. The residual acid chloride was dissolved in 10 ml of methylene chloride. Meanwhile, 1.53 g (4.3 mmols) of deacetylcolchicine and 1.00 g (10 mmols) of triethylamine were dissolved in 40 ml of methylene chloride and cooled to 0° C. The above acid chloride was added dropwise to the mixture, and they were stirred at 0° C. for 1.5 hours and at room temperature for 1.5 hours. The reaction mixture was washed with a sodium hydrogen carbonate aqueous solution and then dried over magnesium sulfate. After the solvent was concentrated, the residue was separated by silica gel column chromatography. By the elution with a benzene-acetone (11:3) solvent, 1.83 g of the above-captioned compound (compound 6) was obtained. The yield was 57%.

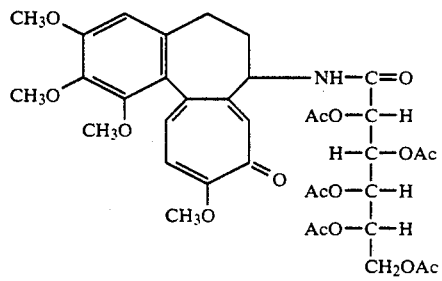

EXAMPLE 8

Deacetylcolchicine-gluconic acid amide (Compound 7)

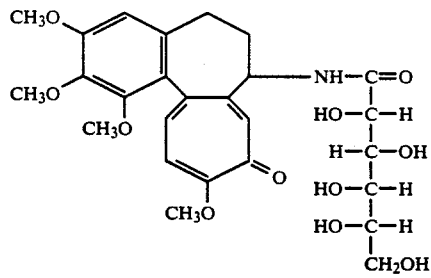

Deacetylcolchicine-gluconic acid pentaacetateamide (compound 6) (3.73 g, 5 mmols) obtained in Example 7 was dissolved in 30 ml of methanol and cooled to 0° C. Five milliliters of 1N sodium hydroxide were added dropwise, and stirring was conducted at 0° C. for 1 hour. The mixture was adjusted to pH of 7 with dilute hydrochloric acid, and concentrated under reduced pressure. Chloroform was added to the residue, and the precipitate was filtered. The filtrate was concentrated and the residue was separated by silica gel column chromatography. As a result, 1.12 g of the above-captioned compound (compound 7) was obtained from a benzene-methanol (5:1) eluted portion. The yield was 42%.

What we claim is:

1. A deacetylcolchicine derivative represented by the formula

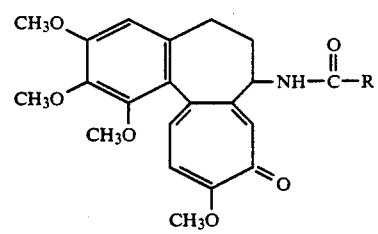

wherein R denotes a residue obtained by removing COOH from a C$_3$–C$_7$ sugar carboxylic acid, and a hydroxyl group present in the residue may properly be protected with a protecting group selected from the group consisting of an acyl group, an acetal group and a ketal group.

2. A deacetylcolchicine derivative of claim 1 wherein R is

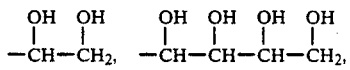

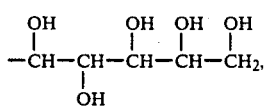

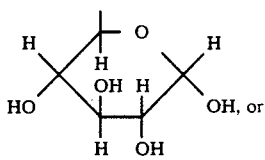

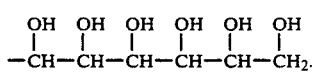

3. A deacetylcolchicine derivative of claim 1 which is selected from deacetylcolchicine-glyceric acid acetonideamide, deacetylcolchicine-glyceric acid amide, deacetylcolchicine-glucuronic acid tetraacetateamide, deacetylcolchicine-glucuronic acid diacetateamide, deacetylcolchicine-glucuronic acid amide, deacetylcolchicine-gluconic acid pentaacetateamide and deacetylcolchicine-gluconic acid amide.

4. A process for producing a deacetylcolchicine derivative of formula (I) recited in claim 1, which comprises subjecting deacetylcolchicine represented by the formula

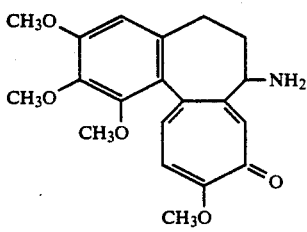

to amidation with a sugar carboxylic acid represented by the formula

R—COOH wherein R is as defined in claim 1, or a reactive derivative thereof selected from the group consisting of a halide and an active ester.

5. A pharmaceutical preparation comprising an antitumor effective amount of a deactylcolchicine derivative of formula (I) recited in claim 1 and a pharmaceutically acceptable carrier or diluent.

6. A process for producing a deacetylcolchicine derivative represented by the formula

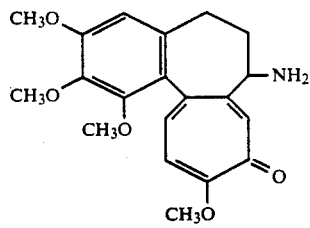
(II)

which comprises reacting colchicine represented by the formula

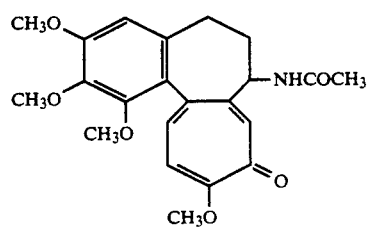
(III)

with trialkyloxonium fluoroborate, and then treating the reaction mixture with water.

* * * * *